US010605596B2

(12) United States Patent
Zhou et al.

(10) Patent No.: US 10,605,596 B2
(45) Date of Patent: Mar. 31, 2020

(54) METHOD AND APPARATUS FOR MEASURING A SIZE OF A CRYSTAL GRAIN, AND METHOD FOR FABRICATING A POLY-SILICON THIN FILM

(71) Applicants: BOE Technology Group Co., Ltd., Beijing (CN); Chengdu BOE Optoelectronics Technology Co., Ltd., Chengdu (CN)

(72) Inventors: Cheng Zhou, Beijing (CN); Zhilong Yuan, Beijing (CN); Xiaodong Yang, Beijing (CN); Chunpeng Zhang, Beijing (CN); Fei Li, Beijing (CN); Yan Hu, Beijing (CN); Hongguang Yuan, Beijing (CN); Chengshih Huang, Beijing (CN); Guowei Su, Beijing (CN); Yu Zhang, Beijing (CN); Zubin Lv, Beijing (CN)

(73) Assignees: BOE Technology Group Co., Ltd., Beijing (CN); Chengdu BOE Optoelectronics Technology Co., Ltd., Chengdu (CN)

( * ) Notice: Subject to any disclaimer, the term of this patent is extended or adjusted under 35 U.S.C. 154(b) by 0 days.

(21) Appl. No.: 16/045,187

(22) Filed: Jul. 25, 2018

(65) Prior Publication Data
US 2019/0086203 A1    Mar. 21, 2019

(30) Foreign Application Priority Data

Sep. 21, 2017    (CN) .......................... 2017 1 0859678

(51) Int. Cl.
*G01B 21/02*     (2006.01)
*H01L 21/02*     (2006.01)
(Continued)

(52) U.S. Cl.
CPC .............. *G01B 21/02* (2013.01); *C30B 1/023* (2013.01); *C30B 29/06* (2013.01); *G01B 11/02* (2013.01);
(Continued)

(58) Field of Classification Search
CPC ........ G01B 21/02; G01N 21/00; G01N 21/84; G01N 2021/0181; G01N 2021/8477
See application file for complete search history.

(56) References Cited

U.S. PATENT DOCUMENTS

| 6,554,972 B1 * | 4/2003 | Ichihara ................. C23C 14/34 204/192.26 |
| 2002/0160586 A1 * | 10/2002 | Wada ..................... G01N 21/95 438/509 |

(Continued)

FOREIGN PATENT DOCUMENTS

| CN | 102130031 | 7/2011 |
| CN | 103185725 | 7/2013 |

(Continued)

OTHER PUBLICATIONS

State Intellectual Property Office of People's Republic of China, "Notification of the First Office Action," issued in connection with Chinese Patent Application No. 201710859678.9, dated Apr. 23, 2019, 14 pages.

*Primary Examiner* — Jonathan M Hansen
(74) *Attorney, Agent, or Firm* — Arent Fox LLP; Michael Fainberg

(57) ABSTRACT

The disclosure discloses a method and apparatus for measuring a size of a crystal grain, and a method for fabricating a poly-silicon thin film. The method for measuring the size of the crystal grain includes: obtaining a grain morphology image of a crystalline region of a crystal, and drawing a grain interface diagram according to the grain morphology image; measuring at least one crystal grain in the grain interface diagram, and determining a transverse size and a longitudinal size of each measured crystal grain; and determining a transverse size and a longitudinal size of a crystal (Continued)

grain of the crystal according to the transverse size and the longitudinal size of each measured crystal grain.

11 Claims, 6 Drawing Sheets

(51) Int. Cl.
    *G01Q 30/02* (2010.01)
    *G01N 23/2251* (2018.01)
    *G01B 11/02* (2006.01)
    *C30B 1/02* (2006.01)
    *G01B 15/00* (2006.01)
    *C30B 29/06* (2006.01)

(52) U.S. Cl.
    CPC ......... *G01B 15/00* (2013.01); *G01N 23/2251* (2013.01); *G01Q 30/02* (2013.01); *H01L 21/02675* (2013.01); *H01L 21/02532* (2013.01); *H01L 21/02595* (2013.01); *H01L 21/02686* (2013.01)

(56) References Cited

U.S. PATENT DOCUMENTS

| 2006/0115685 A1* | 6/2006 | Nakasuga ............. C04B 35/117 |
| | | 428/813 |
| 2016/0016853 A1* | 1/2016 | Yamada ................ C04B 35/486 |
| | | 501/134 |
| 2018/0265990 A1* | 9/2018 | Nanbu ...................... C22F 1/06 |

FOREIGN PATENT DOCUMENTS

| CN | 103529065 | 1/2014 |
| JP | H10122821 | 5/1998 |
| JP | 2004205303 | 7/2004 |
| RU | 2324163 | 10/2007 |

* cited by examiner

METHOD AND APPARATUS FOR MEASURING A SIZE OF A CRYSTAL GRAIN, AND METHOD FOR FABRICATING A POLY-SILICON THIN FILM

CROSS-REFERENCE TO RELATED APPLICATION

This Application claims priority to Chinese Patent Application No. 201710859678.9, filed on Sep. 21, 2017, the content of which is incorporated by reference in the entirety.

TECHNICAL FIELD

This disclosure relates to the field of display technologies, and particularly to a method and apparatus for measuring a size of a crystal grain, and a method for fabricating a poly-silicon thin film.

DESCRIPTION OF THE RELATED ART

A poly-silicon (p-Si) thin film transistor with higher electron mobility than an amorphous-silicon (a-Si) thin film transistor has been widely applied to an array substrate of a display panel. At present, an active layer in the p-Si thin film transistor is typically a poly-silicon thin film formed after an excimer laser annealing process is performed on an a-Si thin film, and the superiority or inferiority of the fabricated poly-silicon thin film may have a significant influence on the electrical performance of the p-Si thin film transistor. Where the superiority or inferiority of the poly-silicon thin film is typically evaluated by measuring a size of a crystal grain of the poly-silicon thin film, and if the measured size of the crystal grain better reflects the geometrical characteristic of the crystal grain, then the superiority or inferiority of the poly-silicon thin film will be better evaluated, so that a fabrication process thereof can be guided to thereby fabricate the p-Si thin film transistor with superior electrical performance.

SUMMARY

Embodiments of the disclosure provide a method and apparatus for measuring a size of a crystal grain, and a method for fabricating a poly-silicon thin film.

In an aspect, the embodiments of the disclosure provide a method for measuring a size of a crystal grain, the method including: obtaining a grain morphology image of a crystalline region of a crystal, and drawing a grain interface diagram according to the grain morphology image; measuring at least one crystal grain in the grain interface diagram, and determining a transverse size and a longitudinal size of each measured crystal grain; and determining a transverse size and a longitudinal size of a crystal grain of the crystal according to the transverse size and the longitudinal size of each measured crystal grain.

In some embodiments, measuring a crystal grain in the grain interface diagram and determining a transverse size of said crystal grain includes: selecting at least one transverse measurement point evenly in a longitudinal interface of said crystal grain in the grain interface diagram; making a transverse measurement of said crystal grain at each selected transverse measurement point to obtain a transverse size of said crystal grain at each selected transverse measurement point; and taking an average of the transverse size of said crystal grain at each selected transverse measurement point as the transverse size of said crystal grain.

In some embodiments, measuring a crystal grain in the grain interface diagram and determining a longitudinal size of said crystal grain includes: selecting at least one longitudinal measurement point evenly in a transverse interface of said crystal grain in the grain interface diagram; making a longitudinal measurement of said crystal grain at each selected longitudinal measurement point to obtain a longitudinal size of said crystal grain at each selected longitudinal measurement point; and taking an average of the longitudinal size of said crystal grain at each selected longitudinal measurement point as the longitudinal size of said crystal grain.

In some embodiments, obtaining the grain morphology image of the crystalline region of the crystal includes: imaging the crystalline region of the crystal using a scanning electron microscope to obtain the grain morphology image of the crystalline region.

In some embodiments, before the at least one crystal grain in the grain interface diagram is measured, the method further includes: screening crystal grains in the grain interface diagram under a set rule to determine valid crystal grains.

Wherein measuring the at least one crystal grain in the grain interface diagram, and determining the transverse size and the longitudinal size of each measured crystal grain includes: measuring at least one valid crystal grain in the grain interface diagram, and determining a transverse size and a longitudinal size of each measured valid crystal grain.

In some embodiments, determining the transverse size and the longitudinal size of the crystal grain of the crystal according to the transverse size and the longitudinal size of each measured crystal grain includes: taking an average of the transverse size of each measured crystal grain in the grain interface diagram as the transverse size of the crystal grain of the crystal; and taking an average of the longitudinal size of each measured crystal grain in the grain interface diagram as the longitudinal size of the crystal grain of the crystal.

In some embodiments, after the transverse size and the longitudinal size of each measured crystal grain in the grain interface diagram are determined, the method further includes: taking an average of the transverse size of each measured crystal grain in the grain interface diagram as a transverse size of a crystal grain in the crystalline region, and taking an average of the longitudinal size of each measured crystal grain in the grain interface diagram as a longitudinal size of the crystal grain in the crystalline region; and determining a transverse size and a longitudinal size of a crystal grain in at least one other crystalline region of the crystal.

Wherein determining the transverse size and the longitudinal size of the crystal grain of the crystal includes: taking an average of transverse sizes of crystal grains in respective crystalline regions as the transverse size of the crystal grain of the crystal; and taking an average of longitudinal sizes of the crystal grains in the respective crystalline regions as the longitudinal size of the crystal grain of the crystal.

In another aspect, the embodiments of the disclosure further provide an apparatus for measuring a size of a crystal grain, the apparatus including: at least one processor and a memory; wherein the memory is configured to store computer readable program codes, the at least one processor is configured to execute the computer readable program codes to: obtain a grain morphology image of a crystalline region of a crystal, and draw a grain interface diagram according to the grain morphology image; measure at least one crystal grain in the grain interface diagram, and determine a transverse size and a longitudinal size of each measured crystal grain; and determine a transverse size and a longitudinal size of a crystal grain of the crystal according to the transverse size and the longitudinal size of each measured crystal grain.

In some embodiments, the at least one processor is further configured to execute the computer readable program codes to: image the crystalline region of the crystal using a scanning electron microscope to obtain the grain morphology image of the crystalline region.

In some embodiments, the at least one processor is further configured to execute the computer readable program codes to: screen crystal grains in the grain interface diagram under a set rule to determine valid crystal grains before the at least one crystal grain in the grain interface diagram is measured; and measure at least one valid crystal grain in the grain interface diagram, and determine a transverse size and a longitudinal size of each measured valid crystal grain.

In some embodiments, the at least one processor is further configured to execute the computer readable program codes to: select at least one transverse measurement point evenly in a longitudinal interface of a crystal grain in the grain interface diagram; make a transverse measurement of said crystal grain at each selected transverse measurement point to obtain a transverse size of said crystal grain at each selected transverse measurement point; and take an average of the transverse size of said crystal grain at each selected transverse measurement point as the transverse size of said crystal grain.

In some embodiments, the at least one processor is further configured to execute the computer readable program codes to: select at least one longitudinal measurement point evenly in a transverse interface of a crystal grain in the grain interface diagram; make a longitudinal measurement of said crystal grain at each selected longitudinal measurement point to obtain a longitudinal size of said crystal grain at each selected longitudinal measurement point; and take an average of the longitudinal size of said crystal grain at each selected longitudinal measurement point as the longitudinal size of said crystal grain.

In some embodiments, the at least one processor is further configured to execute the computer readable program codes to: take an average of the transverse size of each measured crystal grain in the grain interface diagram as the transverse size of the crystal grain of the crystal; and take an average of the longitudinal size of each measured crystal grain in the grain interface diagram as the longitudinal size of the crystal grain of the crystal.

In some embodiments, the at least one processor is further configured to execute the computer readable program codes to: obtain a grain morphology image of at least one other crystalline region of the crystal, and draw a grain interface diagram of each of the at least one other crystalline region according to the grain morphology image of the at least one other crystalline region; measure at least one crystal grain in the grain interface diagram of each of the at least one other crystalline region, and determine a transverse size and a longitudinal size of each measured crystal grain in the grain interface diagram of each of the at least one other crystalline region; take an average of a transverse size of each measured crystal grain in a grain interface diagram of each crystalline region as a transverse size of a crystal grain in said crystalline region, and take an average of a longitudinal size of each measured crystal grain in the grain interface diagram of each crystalline region as a longitudinal size of the crystal grain in said crystalline region; and take an average of transverse sizes of crystal grains in respective crystalline regions as the transverse size of the crystal grain of the crystal, and take an average of longitudinal sizes of crystal grains in respective crystalline regions as the longitudinal size of the crystal grain of the crystal.

In still another aspect, the embodiments of the disclosure further provide a method for fabricating a poly-silicon thin film, the method including: determining a transverse size and a longitudinal size of a crystal grain of the poly-silicon thin film, using the method above for measuring a size of a crystal grain according to the embodiments of the disclosure, wherein the poly-silicon thin film is fabricated using a current process parameter of an excimer laser annealing process; determining a process evaluation value of the poly-silicon thin film according to the transverse size and the longitudinal size of the crystal grain of the poly-silicon thin film; determining an adjusted process parameter of the excimer laser annealing process according to the process evaluation value, and a set correspondence relationship between process evaluation values and adjusted process parameters; and adjusting the current process parameter of the excimer laser annealing process to the adjusted process parameter, and subjecting an amorphous-silicon thin film to the excimer laser annealing process using the adjusted process parameter to form the poly-silicon thin film.

In some embodiments, the process evaluation value is one or a combination of a difference between the transverse size and the longitudinal size of the crystal grain of the poly-silicon thin film, and a difference between an average of the transverse size and the longitudinal size of the crystal grain of the poly-silicon thin film, and a process specification value.

BRIEF DESCRIPTION OF THE DRAWINGS

In order to make the technical solutions according to embodiments of the disclosure more apparent, the drawings to which a description of the embodiments refers will be briefly introduced below, and apparently the drawings to be described below are merely illustrative of some of the embodiments of the disclosure, and those ordinarily skilled in the art can derive from these drawings other drawings without any inventive effort.

DETAILED DESCRIPTION OF THE EMBODIMENTS

Figure 1:
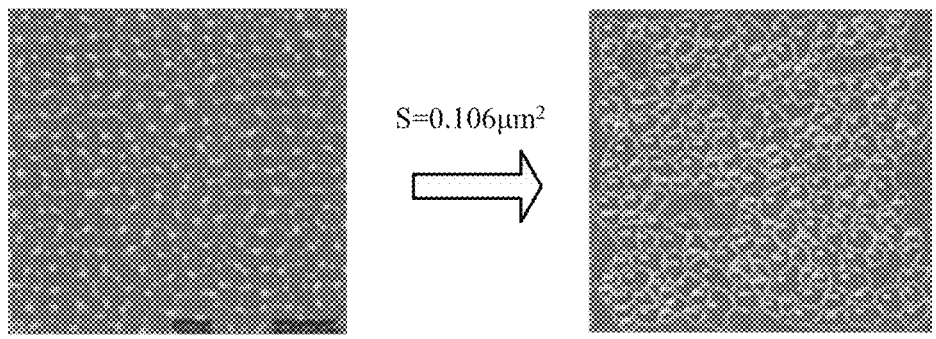
FIG. 1 is a schematic diagram of measuring a size of a crystal grain of an irregularly shaped poly-silicon thin film in the related art.
Figure 2:
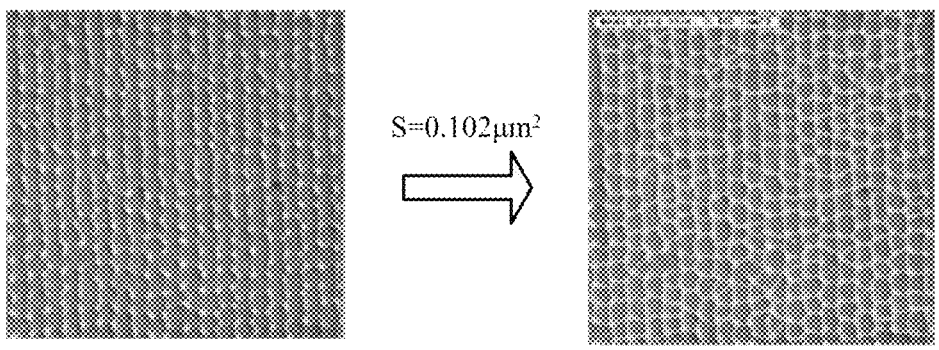
FIG. 2 is a schematic diagram of measuring a size of a crystal grain of a poly-silicon thin film with a tetragonal crystal structure in the related art.

At present, a size of a crystal grain of a poly-silicon thin film is typically measured by making a statistic of an average area of crystal grains in a grain interface diagram, but the average area of the crystal grains may not well reflect the geometrical characteristic of the crystal grains. For example, a size of a crystal grain of an irregularly shaped poly-silicon thin film (as illustrated in FIG. 1), and a size of a crystal grain of a poly-silicon thin film with a tetragonal crystal structure (as illustrated in FIG. 2) are measured respectively as describe above, and their average areas of crystal grains as a result of making a statistic thereof are 0.106 $\mu m^2$ and 0.102 $\mu m^2$; and although their average areas of crystal grains are substantially the same, they really represent two different types of p-Si crystal grains, so a fabrication process thereof cannot be guided in effect, and thus a p-Si thin film transistor with superior electrical performance cannot be fabricated.

Embodiments of the disclosure provide a method and apparatus for measuring a size of a crystal grain, and a method for fabricating a poly-silicon thin film so as to enable the measured size of the crystal grain to well reflect a geometrical characteristic of the crystal grain to thereby guide in effect a fabrication process.

The technical solutions according to the embodiments of the disclosure will be described clearly and fully with reference to the drawings in the embodiments of the disclosure, and apparently the embodiments to be described are only a part but not all of the embodiments of the disclosure. Based upon the embodiments here of the disclosure, all the other embodiments which can occur to those ordinarily skilled in the art without any inventive effort shall fall into the scope of the disclosure.

It shall be noted that the thicknesses and shapes of respective layers in the drawings are not intended to reflect any real proportion, but only intended to illustrate the content of the disclosure.

Figure 3:
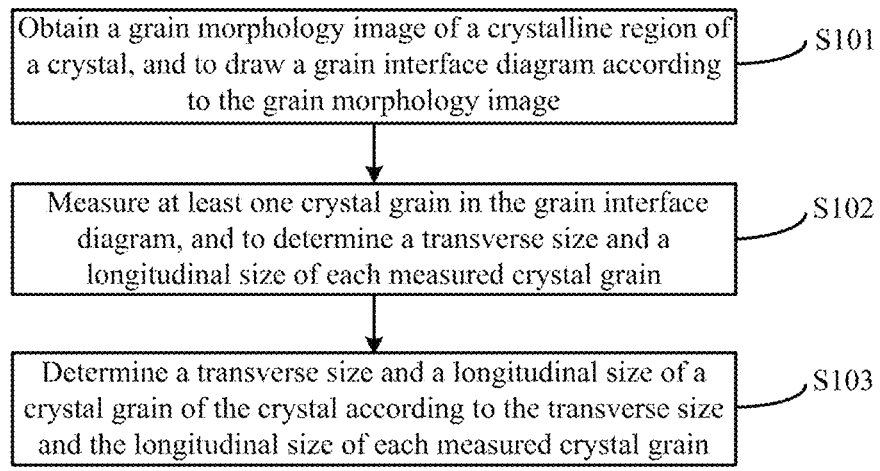
FIG. 3 is a schematic flow chart of a method for measuring a size of a crystal grain according to the embodiments of the disclosure.

As illustrated in FIG. 3, a method for measuring a size of a crystal grain according to the embodiments of the disclosure includes the following operations.

S101 is to obtain a grain morphology image of a crystalline region of a crystal, and to draw a grain interface diagram according to the grain morphology image.

Here the grain interface diagram is drawn according to the grain morphology image by drawing the grain interface diagram using grayscale differences in the grain morphology image, for example, although the embodiments of the disclosure will not be limited thereto.

S102 is to measure at least one crystal grain in the grain interface diagram, and to determine a transverse size and a longitudinal size of each measured crystal grain.

S103 is to determine a transverse size and a longitudinal size of a crystal grain of the crystal according to the transverse size and the longitudinal size of each measured crystal grain.

In the method above for measuring a size of a crystal grain according to the embodiments of the disclosure, the transverse size and the longitudinal size of the crystal grain of the crystal can be determined, and the transverse size and the longitudinal size of the crystal grain of the crystal can well reflect a geometrical characteristic of the crystal grain to thereby guide in effect a fabrication process.

In some embodiments, the grain morphology image of the crystalline region of the crystal is obtained in the operation S101 via a following operation: imaging the crystalline region of the crystal using a Scanning Electron Microscope (SEM) to obtain the grain morphology image of the crystalline region.

It shall be noted that although the grain morphology image of the crystalline region of the crystal may be obtained using a Scanning Electron Microscope (SEM), the embodiments of the disclosure will not be limited thereto; and for example, the grain morphology image of the crystalline region of the crystal may alternatively be obtained using an atomic force microscope, a Laser co-focus microscope, etc.

In some embodiments, a crystal grain in the grain interface diagram is measured and a transverse size of said crystal grain is determined, in the operation S102 via following operations.

Selecting at least one transverse measurement point evenly in a longitudinal interface of said crystal grain in the grain interface diagram; making a transverse measurement of said crystal grain at each selected transverse measurement point to obtain a transverse size of said crystal grain at each selected transverse measurement point; and taking an average of the transverse size of said crystal grain at each selected transverse measurement point as the transverse size of said crystal grain.

Here the transverse size of said crystal grain can be determined by selecting one transverse measurement point, but in order to lower an error, and to improve the accuracy of measurement, a plurality of transverse measurement points can be selected for determining the transverse size of said crystal grain, although the embodiments of the disclosure will not be limited thereto.

For example, the longitudinal interface of said crystal grain in the grain interface diagram is divided by $2^n$ times evenly, and transverse sizes at respective transverse measurement points are obtained as $l_{x1}$, $l_{x2}$, $l_{x3}$ . . . $l_{x(2^n-1)}$ respectively, so the transverse size of said crystal grain is calculated in an Equation (1) of:

$$L_x = \frac{l_{x1} + l_{x2} + l_{x3} + K + l_{x(2^n-1)}}{2^n - 1}.$$

Where a value of n is selected flexibly under a practical condition.

In some embodiments, a crystal grain in the grain interface diagram is measured and a longitudinal size of said crystal grain is determined, in the operation S102 via following operations.

Selecting at least one longitudinal measurement point evenly in a transverse interface of said crystal grain in the grain interface diagram; making a longitudinal measurement of said crystal grain at each selected longitudinal measurement point to obtain a longitudinal size of said crystal grain at each selected longitudinal measurement point; and taking an average of the longitudinal size of said crystal grain at each selected longitudinal measurement point as the longitudinal size of said crystal grain.

Here the longitudinal size of said crystal grain can be determined by selecting one longitudinal measurement point, but in order to lower an error, and to improve the accuracy of measurement, a plurality of longitudinal measurement points can be selected for determining the longitudinal size of said crystal grain, although the embodiments of the disclosure will not be limited thereto.

For example, the transverse interface of said crystal grain in the grain interface diagram is divided by $2^n$ times evenly, and longitudinal sizes at respective longitudinal measurement points are obtained as $l_{y1}, l_{y2}, l_{y3} \ldots l_{y(2^n-1)}$ respectively, so the longitudinal size of said crystal grain is calculated in an Equation (2) of:

$$L_y = \frac{l_{y1} + l_{y2} + l_{y3} + K + l_{y(2^n-1)}}{2^n - 1}.$$

Where the value of n is selected flexibly under a practical condition.

In some embodiments, the transverse size and the longitudinal size of the crystal grain are determined by selecting a plurality of measurement points evenly.

Figure 4:
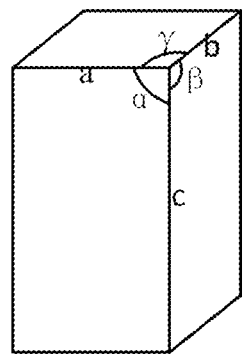
FIG. 4 is a schematic structural diagram of a crystal cell of a tetragonal crystal according to the embodiments of the disclosure.
Figure 5:
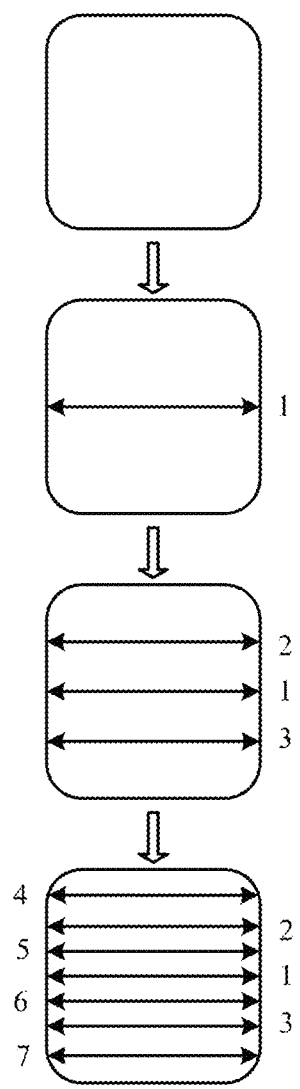
FIG. 5 is a schematic flow chart of determining a transverse size of a crystal grain in the method for measuring a size of a crystal grain according to the embodiments of the disclosure.
Figure 6:
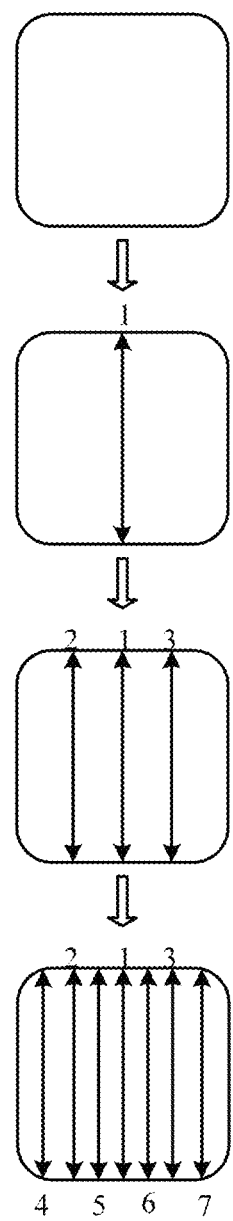
FIG. 6 is a schematic flow chart of determining a longitudinal size of a crystal grain in the method for measuring a size of a crystal grain according to the embodiments of the disclosure.

For example, the crystal is a poly-silicon thin film with a tetragonal crystal structure, and a crystal cell structure of the tetragonal crystal is typically as illustrated in FIG. 4, where parameters of the crystal cell are as follows: a=b≠c, and α=β=γ=90°; and as illustrated in FIG. 5, the transverse size of the crystal grain is determined by selecting a plurality of measurement points evenly in the following operations.

(1) A longitudinal bisectional point of the crystal grain is selected, and a transverse size is measured as $l_{x1}$.

(2) Longitudinal quarter points of the crystal grain are selected, and transverse sizes are measured as $l_{x2}, l_{x3}$.

(3) Longitudinal eighth points of the crystal grain are selected, and transverse sizes are measured as $l_{x4}, l_{x5}, l_{x6}, l_{x7}$.

(4) The transverse size of the crystal grain is calculated as $$L_x = \frac{l_{x1} + l_{x2} + l_{x3} + l_{x4} + l_{x5} + l_{x6} + l_{x7}}{7}.$$

Alike the longitudinal size of the crystal grain is calculated as $$L_y = \frac{l_{y1} + l_{y2} + l_{y3} + l_{y4} + l_{y5} + l_{y6} + l_{y7}}{7}.$$

It shall be noted that the method for measuring a size of a crystal grain according to the embodiments of the disclosure is not only applicable to a tetragonal crystal, but also applicable to a cubic crystal, an orthogonal crystal, etc.

In some embodiments, before the at least one crystal grain in the grain interface diagram is measured, the method further includes: screening crystal grains in the grain interface diagram under a set rule to determine valid crystal grains.

Here the set rule includes screening out a crystal grain with an incomplete crystal grain boundary in the grain interface diagram, or screening out a crystal grain with an abnormal crystal grain size in the grain interface diagram, or a combination of both, for example.

Accordingly, the at least one crystal grain in the grain interface diagram is measured and the transverse size and the longitudinal size of each measured crystal grain are determined, in the operation S102 via a following operation: measuring at least one valid crystal grain in the grain interface diagram, and determining a transverse size and a longitudinal size of each measured valid crystal grain.

In the method above for measuring a size of a crystal grain according to the embodiments of the disclosure, only the valid crystal grain(s) are measured, so that the accuracy of measurement can be improved.

It shall be noted that in the embodiments of the disclosure, the transverse size and the longitudinal size of any crystal grain can alternatively be determined instead of only the transverse size(s) and the longitudinal size(s) of the valid crystal grain(s), although the embodiments of the disclosure will not be limited thereto.

Next, implementations of the operation S103 to determine the transverse size and the longitudinal size of the crystal grain of the crystal according to the transverse size and the longitudinal size of each measured crystal grain will be described below.

In some embodiments, the transverse size and the longitudinal size of the crystal grain of the crystal are determined according to the transverse size and the longitudinal size of each measured crystal grain via following operations.

Taking an average of the transverse size of each measured crystal grain in the grain interface diagram as the transverse size of the crystal grain of the crystal; and taking an average of the longitudinal size of each measured crystal grain in the grain interface diagram as the longitudinal size of the crystal grain of the crystal.

Here in an extreme instance, when only one crystal grain in the grain interface diagram is measured, the transverse size of said crystal grain in the grain interface diagram can be taken as the transverse size of the crystal grain of the crystal, and the longitudinal size of said crystal grain in the grain interface diagram can be taken as the longitudinal size of the crystal grain of the crystal.

In this method for measuring a size of a crystal grain according to the embodiments of the disclosure, the average of the transverse size of each measured crystal grain in the grain interface diagram is taken as the transverse size of the crystal grain of the crystal, and the average of the longitudinal size of each measured crystal grain in the grain interface diagram is taken as the longitudinal size of the crystal grain of the crystal, so the determined transverse size and longitudinal size of the crystal grain of the crystal are well representative, thus well reflecting a geometrical characteristic of the crystal grain.

In some embodiments, after the transverse size and the longitudinal size of each measured crystal grain in the grain interface diagram are determined, the method further includes the following operations.

Taking an average of the transverse size of each measured crystal grain in the grain interface diagram as a transverse size of a crystal grain in the crystalline region, and taking an average of the longitudinal size of each measured crystal grain in the grain interface diagram as a longitudinal size of the crystal grain in the crystalline region; and determining a transverse size and a longitudinal size of a crystal grain in at least one other crystalline region of the crystal.

Accordingly, the transverse size and the longitudinal size of the crystal grain of the crystal are determined via following operations.

Taking an average of transverse sizes of crystal grains in respective crystalline regions as the transverse size of the crystal grain of the crystal; and taking an average of longitudinal sizes of the crystal grains in the respective crystalline regions as the longitudinal size of the crystal grain of the crystal.

In this method for measuring a size of a crystal grain according to the embodiments of the disclosure, the average of the transverse sizes of the crystal grains in the respective crystalline regions is taken as the transverse size of the crystal grain of the crystal, and the average of the longitudinal sizes of the crystal grain in the respective crystalline regions is taken as the longitudinal size of the crystal grain of the crystal, so the determined transverse size and longitudinal size of the crystal grain of the crystal are more representative, thus well reflecting a geometrical characteristic of the crystal grain.

Figure 7:
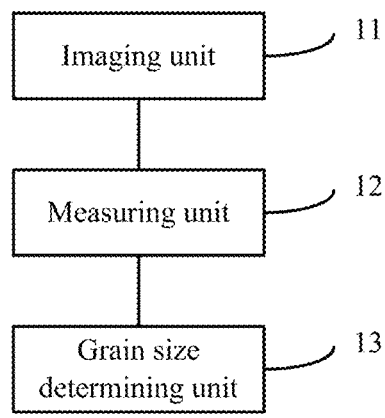
FIG. 7 is a schematic structural diagram of an apparatus for measuring a size of a crystal grain according to the embodiments of the disclosure.

Based upon the same inventive concept, as illustrated in FIG. 7, the embodiments of the disclosure further provide an apparatus for measuring a size of a crystal grain, where the apparatus includes following components.

An imaging unit 11 is configured to obtain a grain morphology image of a crystalline region of a crystal, and draw a grain interface diagram according to the grain morphology image.

A measuring unit 12 is configured to measure at least one crystal grain in the grain interface diagram, and determine a transverse size and a longitudinal size of each measured crystal grain.

A grain size determining unit 13 is configured to determine a transverse size and a longitudinal size of a crystal grain of the crystal according to the transverse size and the longitudinal size of each measured crystal grain.

In some embodiments, the imaging unit 11 is configured to image the crystalline region of the crystal using a scanning electron microscope to obtain the grain morphology image of the crystalline region.

Figure 8:
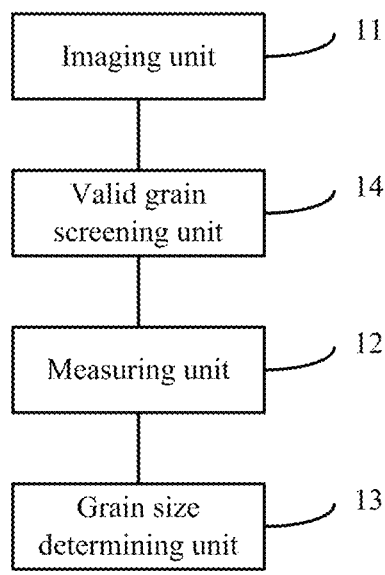
FIG. 8 is another schematic structural diagram of the apparatus for measuring a size of a crystal grain according to the embodiments of the disclosure.

In some embodiments, as illustrated in FIG. 8, the apparatus further includes a valid grain screening unit 14 configured to screen crystal grains in the grain interface diagram under a set rule to determine valid crystal grains, before the measuring unit 12 measures the at least one crystal grain in the grain interface diagram.

According, the measuring unit 12 is configured to measure at least one valid crystal grain in the grain interface diagram, and determine a transverse size and a longitudinal size of each measured valid crystal grain.

In some embodiments, the measuring unit 12 is configured to select at least one transverse measurement point evenly in a longitudinal interface of a crystal grain in the grain interface diagram; make a transverse measurement of said crystal grain at each selected transverse measurement point to obtain a transverse size of said crystal grain at each selected transverse measurement point; and take an average of the transverse size of said crystal grain at each selected transverse measurement point as the transverse size of said crystal grain.

In some embodiments, the measuring unit 12 is configured to select at least one longitudinal measurement point evenly in a transverse interface of a crystal grain in the grain interface diagram; make a longitudinal measurement of said crystal grain at each selected longitudinal measurement point to obtain a longitudinal size of said crystal grain at each selected longitudinal measurement point; and take an average of the longitudinal size of said crystal grain at each selected longitudinal measurement point as the longitudinal size of said crystal grain.

In some embodiments, the grain size determining unit 13 is configured to take an average of the transverse size of each measured crystal grain in the grain interface diagram as the transverse size of the crystal grain of the crystal; and take an average of the longitudinal size of each measured crystal grain in the grain interface diagram as the longitudinal size of the crystal grain of the crystal.

In some embodiments, the imaging 11 is further configured to obtain a grain morphology image of at least one other crystalline region of the crystal, and draw a grain interface diagram of each of the at least one other crystalline region according to the grain morphology image of the at least one other crystalline region.

The measuring unit 12 is further configured to measure at least one crystal grain in the grain interface diagram of each of the at least one other crystalline region, and determine a transverse size and a longitudinal size of each measured crystal grain in the grain interface diagram of each of the at least one other crystalline region.

The grain size determining unit 13 is further configured to take an average of a transverse size of each measured crystal grain in a grain interface diagram of each crystalline region as a transverse size of a crystal grain in said crystalline region, and take an average of a longitudinal size of each measured crystal grain in the grain interface diagram of each crystalline region as a longitudinal size of the crystal grain in said crystalline region; and take an average of transverse sizes of crystal grains in respective crystalline regions as the transverse size of the crystal grain of the crystal, and take an average of longitudinal sizes of crystal grains in respective crystalline regions as the longitudinal size of the crystal grain of the crystal.

Figure 9:
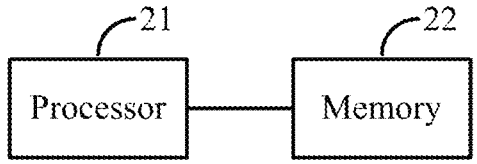
FIG. 9 is a schematic structural diagram of another apparatus for measuring a size of a crystal grain according to the embodiments of the disclosure.
Figure 10:
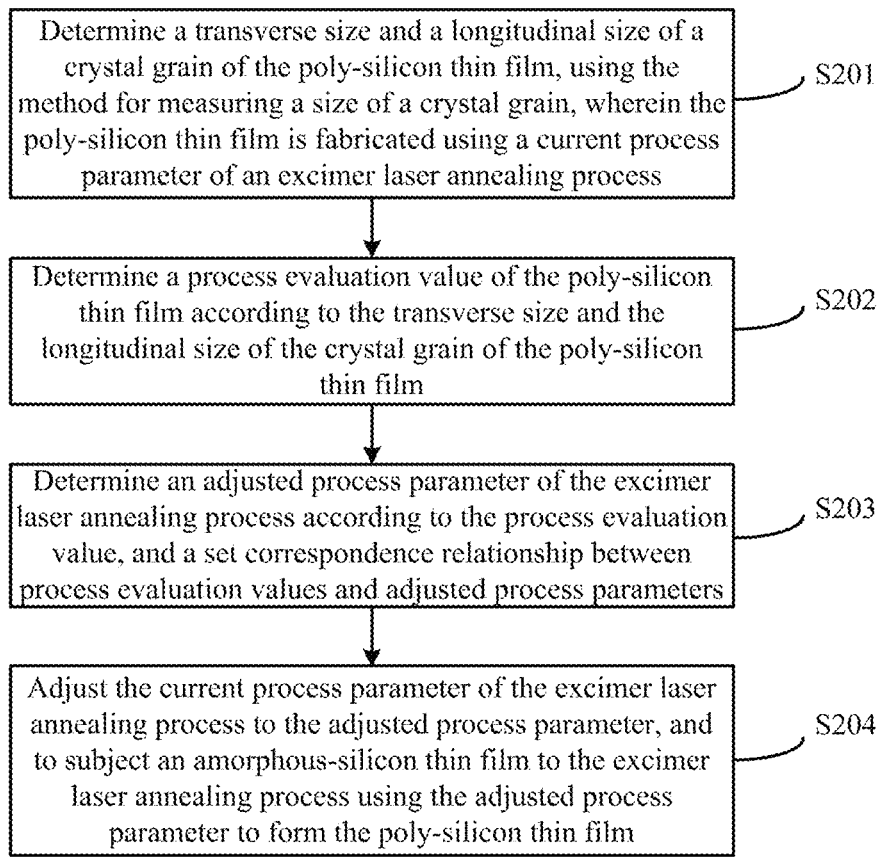
FIG. 10 is a schematic flow chart of a method for fabricating a poly-silicon thin film according to the embodiments of the disclosure.

Based upon the same inventive concept, as illustrated in FIG. 9, the embodiments of the disclosure further provide another apparatus for measuring a size of a crystal grain, where the apparatus includes at least one processor 21 and a memory 22; wherein the memory 22 is configured to store computer readable program codes, the at least one processor 21 is configured to execute the computer readable program codes to: obtain a grain morphology image of a crystalline region of a crystal, and draw a grain interface diagram according to the grain morphology image; measure at least one crystal grain in the grain interface diagram, and determine a transverse size and a longitudinal size of each measured crystal grain; and determine a transverse size and a longitudinal size of a crystal grain of the crystal according to the transverse size and the longitudinal size of each measured crystal grain.

In some embodiments, the at least one processor 21 is further configured to execute the computer readable program codes to: image the crystalline region of the crystal using a scanning electron microscope to obtain the grain morphology image of the crystalline region.

In some embodiments, the at least one processor 21 is further configured to execute the computer readable program codes to: screen crystal grains in the grain interface diagram under a set rule to determine valid crystal grains before the at least one crystal grain in the grain interface diagram is measured; and measure at least one valid crystal grain in the grain interface diagram, and determine a transverse size and a longitudinal size of each measured valid crystal grain.

In some embodiments, the at least one processor 21 is further configured to execute the computer readable program codes to: select at least one transverse measurement point evenly in a longitudinal interface of a crystal grain in the grain interface diagram; make a transverse measurement of said crystal grain at each selected transverse measurement point to obtain a transverse size of said crystal grain at each selected transverse measurement point; and take an average of the transverse size of said crystal grain at each selected transverse measurement point as the transverse size of said crystal grain.

In some embodiments, the at least one processor 21 is further configured to execute the computer readable program codes to: select at least one longitudinal measurement point evenly in a transverse interface of a crystal grain in the grain interface diagram; make a longitudinal measurement of said crystal grain at each selected longitudinal measurement point to obtain a longitudinal size of said crystal grain at each selected longitudinal measurement point; and take an average of the longitudinal size of said crystal grain at each selected longitudinal measurement point as the longitudinal size of said crystal grain.

In some embodiments, the at least one processor 21 is further configured to execute the computer readable program codes to: take an average of the transverse size of each measured crystal grain in the grain interface diagram as the transverse size of the crystal grain of the crystal; and take an average of the longitudinal size of each measured crystal grain in the grain interface diagram as the longitudinal size of the crystal grain of the crystal.

In some embodiments, the at least one processor 21 is further configured to execute the computer readable program codes to: obtain a grain morphology image of at least one other crystalline region of the crystal, and draw a grain interface diagram of each of the at least one other crystalline region according to the grain morphology image of the at least one other crystalline region; measure at least one crystal grain in the grain interface diagram of each of the at least one other crystalline region, and determine a transverse size and a longitudinal size of each measured crystal grain in the grain interface diagram of each of the at least one other crystalline region; take an average of a transverse size of each measured crystal grain in a grain interface diagram of each crystalline region as a transverse size of a crystal grain in said crystalline region, and take an average of a longitudinal size of each measured crystal grain in the grain interface diagram of each crystalline region as a longitudinal size of the crystal grain in said crystalline region; and take an average of transverse sizes of crystal grains in respective crystalline regions as the transverse size of the crystal grain of the crystal, and take an average of longitudinal sizes of crystal grains in respective crystalline regions as the longitudinal size of the crystal grain of the crystal.

Based upon the same inventive concept, as illustrated in FIG. 9, the embodiments of the disclosure further provide a method for fabricating a poly-silicon thin film, where the method includes the following operations.

S201 is to determine a transverse size and a longitudinal size of a crystal grain of the poly-silicon thin film, using the method above for measuring a size of a crystal grain according to the embodiments of the disclosure, wherein the poly-silicon thin film is fabricated using a current process parameter of an excimer laser annealing process.

Here the process parameter of the excimer laser annealing process includes a crystallization period of time, laser energy, etc.

S202 is to determine a process evaluation value of the poly-silicon thin film according to the transverse size and the longitudinal size of the crystal grain of the poly-silicon thin film.

Here the process evaluation value is one or a combination of a difference between the transverse size and the longitudinal size of the crystal grain of the poly-silicon thin film, and a difference between an average of the transverse size and the longitudinal size of the crystal grain of the poly-silicon thin film, and a process specification value (spec value). Where the process evaluation value can be used to evaluate the process, and for example, the difference between the transverse size and the longitudinal size of the crystal grain can be used to evaluate the regularity of the crystal grain, and when the transverse size of the crystal grain is equal to the longitudinal size thereof, there is the highest regularity of the crystal grain.

S203 is to determine an adjusted process parameter of the excimer laser annealing process according to the process evaluation value, and a set correspondence relationship between process evaluation values and adjusted process parameters.

Here the set correspondence relationship between the process evaluation values and the adjusted process parameters can be created from a number of experimental measurements, for example.

S204 is to adjust the current process parameter of the excimer laser annealing process to the adjusted process parameter, and to subject an amorphous-silicon thin film to the excimer laser annealing process using the adjusted process parameter to form the poly-silicon thin film.

In the method for fabricating a poly-silicon thin film according to the embodiments of the disclosure, since the transverse size and the longitudinal size of the crystal grain of the poly-silicon thin film, fabricated using the current process parameter of the excimer laser annealing process, are determined using the method above for measuring a size of a crystal grain, the transverse size and the longitudinal size of the crystal grain of the poly-silicon thin film can well reflect the geometrical characteristic of the crystal grain, so the determined process evaluation value of the poly-silicon thin film can be determined accurately according to the transverse size and the longitudinal size of the crystal grain of the poly-silicon thin film, then the adjusted process parameter of the excimer laser annealing process also be determined accurately according to the set correspondence relationship between the process evaluation values and the adjusted process parameters, and the process parameter of the excimer laser annealing process can be adjusted to the accurate adjusted process parameter, so that the superior poly-silicon thin film can be fabricated using the adjusted process parameter, that is, the fabrication process can be guided in effect.

In addition, after a transverse size and a longitudinal size of any valid crystal grain in a crystalline region are determined, a product of the transverse size and the longitudinal size of the valid crystal grain can be taken as an area of the valid crystal grain. And then a sum of areas of respective valid crystal grains in the crystalline region can be calculated, and a ratio of the sum of the areas of the respective valid crystal grains in the crystalline region to an imaging area of the crystalline region can be calculated as a proportion of the valid crystal grains in the crystalline region, and a crystallization proportion of the poly-silicon thin film can be determined according to the proportion of the valid crystal grains, so that the process parameter can be adjusted according to the crystallization proportion.

Of course, the proportions of valid crystal grains in a plurality of crystalline regions can be calculated, then the average of the proportions of valid crystal grains in the respective crystalline regions can be calculated, and next a crystallization proportion of the poly-silicon thin film can be determined according to the average of the proportions of valid crystal grains, so that the process parameter can be adjusted according to the crystallization proportion.

In summary, in the technical solutions according to the embodiments of the disclosure, firstly a grain morphology image of a crystalline region of a crystal is obtained, and a grain interface diagram is drawn according to the grain morphology image; then at least one crystal grain in the grain interface diagram is measured, and a transverse size and a longitudinal size of each measured crystal grain are determined respectively; and next a transverse size and a longitudinal size of the crystal grain of the crystal are determined according to the transverse size and the longitudinal size of each measured crystal grain. In this way, the transverse size and the longitudinal size of the crystal grain of the crystal can be determined, and the transverse size and the longitudinal size of the crystal grain of the crystal can well reflect a geometrical characteristic of the crystal grain to thereby guide in effect a fabrication process.

Evidently those skilled in the art can make various modifications and variations to the disclosure without departing from the spirit and scope of the disclosure. Thus the disclosure is also intended to encompass these modifications and variations thereto so long as the modifications and variations come into the scope of the claims appended to the disclosure and their equivalents.

The invention claimed is:

1. A method for measuring a size of a crystal grain, the method comprising:
    obtaining a grain morphology image of a crystalline region of a crystal, and drawing a grain interface diagram according to the grain morphology image;
    selecting at least one transverse measurement point evenly in a longitudinal interface of at least one crystal grain in a grain interface diagram;
    making a transverse measurement of the at least one crystal grain at each selected transverse measurement point to obtain a transverse size of the at least one crystal grain at each selected transverse measurement point;
    taking an average of the transverse size of the at least one crystal grain at each selected transverse measurement point as the transverse size of the at least one crystal grain;
    selecting at least one longitude measurement point evenly in a transverse interface of the at least one crystal grain in the grain interface diagram;
    making a longitudinal measurement of the a least one crystal grain at each selected longitudinal measurement point to obtain a longitudinal size of the at least one crystal grain at each selected longitudinal measurement point;
    taking an average of the longitudinal size of the at least one crystal grain at each selected longitudinal measurement point as the longitudinal size of the at least one crystal grain;
    taking an average of the transverse size of each measured crystal grain in the grain interface diagram as the transverse size of the crystal grain of the crystal; and
    taking an average of the longitudinal size of the each measured crystal grain in the grain interface diagram as the longitudinal size of the crystal grain of the crystal.

2. The method according to claim 1, wherein obtaining the grain morphology image of the crystalline region of the crystal comprises:
    imaging the crystalline region of the crystal using a scanning electron microscope to obtain the grain morphology image of the crystalline region.

3. The method according to claim 1, wherein before the at least one crystal grain in the grain interface diagram is measured, the method further comprises:
    screening crystal grains in the grain interface diagram under a set rule to determine valid crystal grains;
    wherein measuring the at least one crystal grain in the grain interface diagram, and determining the transverse size and the longitudinal size of each measured crystal grain comprises:
    measuring at least one valid crystal grain in the grain interface diagram, and determining a transverse size and a longitudinal size of each measured valid crystal grain.

4. The method according to claim 1, wherein after the transverse size and the longitudinal size of each measured crystal grain in the grain interface diagram are determined, the method further comprises:
    taking an average of the transverse size of each measured crystal grain in the grain interface diagram as a transverse size of a crystal grain in the crystalline region, and taking an average of the longitudinal size of each measured crystal grain in the grain interface diagram as a longitudinal size of the crystal grain in the crystalline region; and
    determining a transverse size and a longitudinal size of a crystal grain in at least one other crystalline region of the crystal;
    wherein determining the transverse size and the longitudinal size of the crystal grain of the crystal comprises:
    taking an average of transverse sizes of crystal grains in respective crystalline regions as the transverse size of the crystal grain of the crystal; and
    taking an average of longitudinal sizes of the crystal grains in the respective crystalline regions as the longitudinal size of the crystal grain of the crystal.

5. An apparatus for measuring a size of a crystal grain, the apparatus comprising at least one processor and a memory; wherein the memory is configured to store computer readable program codes, the at least one processor is configured to execute the computer readable program codes to:
    obtain a grain morphology image of a crystalline region of a crystal, and draw a grain interface diagram according to the grain morphology image;
    select at least one transverse measurement point evenly in a longitudinal interface of a crystal grain in a grain interface diagram;
    make a transverse measurement of the crystal grain at each selected transverse measurement point to obtain a transverse size of the crystal grain at each selected transverse measurement point; and
    take an average of the transverse size of the crystal grain at each selected transverse measurement point as the transverse size of the crystal grain;
    select at least one longitudinal measurement point evenly in a transverse interface of a crystal grain in the grain interface diagram;
    make a longitudinal measurement of the crystal grain at each selected longitudinal measurement point to obtain a longitudinal size of the crystal grain at each selected longitudinal measurement point;
    take an average of the longitudinal size of the crystal grain at each selected longitudinal measurement point as the longitudinal size of the crystal grain;
    take an average of the transverse size of each measured crystal grain in the grain interface diagram as the transverse size of the crystal grain of the crystal; and
    take an average of the longitudinal size of each measured crystal grain in the grain interface diagram as the longitudinal size of the crystal grain of the crystal.

6. The apparatus according to claim 5, wherein the at least one processor is further configured to execute the computer readable program codes to:

image the crystalline region of the crystal using a scanning electron microscope to obtain the grain morphology image of the crystalline region.

7. The apparatus according to claim 5, wherein the at least one processor is further configured to execute the computer readable program codes to:
screen crystal grains in the grain interface diagram under a set rule to determine valid crystal grains before the at least one crystal grain in the grain interface diagram is measured; and
measure at least one valid crystal grain in the grain interface diagram, and determine a transverse size and a longitudinal size of each measured valid crystal grain.

8. The apparatus according to claim 6, wherein the at least one processor is further configured to execute the computer readable program codes to:
screen crystal grains in the grain interface diagram under a set rule to determine valid crystal grains before the at least one crystal grain in the grain interface diagram is measured; and
measure at least one valid crystal grain in the grain interface diagram, and determine a transverse size and a longitudinal size of each measured valid crystal grain.

9. The apparatus according to claim 5, wherein the at least one processor is further configured to execute the computer readable program codes to:
obtain a grain morphology image of at least one other crystalline region of the crystal, and draw a grain interface diagram of each of the at least one other crystalline region according to the grain morphology image of the at least one other crystalline region;
measure at least one crystal grain in the grain interface diagram of each of the at least one other crystalline region, and determine a transverse size and a longitudinal size of each measured crystal grain in the grain interface diagram of each of the at least one other crystalline region;
take an average of a transverse size of each measured crystal grain in a grain interface diagram of each crystalline region as a transverse size of a crystal grain in said crystalline region, and take an average of a longitudinal size of each measured crystal grain in the grain interface diagram of each crystalline region as a longitudinal size of the crystal grain in said crystalline region; and
take an average of transverse sizes of crystal grains in respective crystalline regions as the transverse size of the crystal grain of the crystal, and take an average of longitudinal sizes of crystal grains in respective crystalline regions as the longitudinal size of the crystal grain of the crystal.

10. A method for fabricating a poly-silicon thin film, the method comprising:
obtaining a grain morphology image of a crystalline region of a crystal, and drawing a grain interface diagram according to the grain morphology image;
selecting at least one transverse measurement point evenly in a longitudinal interface of at least one crystal grain of the poly-silicon thin film in a grain interface diagram, wherein the poly-silicon thin film is fabricated using a current process parameter of an excimer laser annealing process;
making a transverse measurement of the at least one crystal grain at each selected transverse measurement point to obtain transverse size of the at least one crystal grain at each selected transverse measurement point;
taking an average of the transverse size of the at least one crystal grain at each selected transverse measurement point as the transverse size of the at least one crystal grain;
selecting at least one longitudinal measurement point evenly in a transverse interface of the least one crystal grain in the grain interface diagram;
making a longitudinal measurement of the at least one crystal grain at each selected longitudinal measurement point to obtain a longitudinal size of the at least one crystal grain at each selected longitudinal measurement point;
taking an average of the longitudinal size of the at least one crystal grain at each selected longitudinal measurement point as the longitudinal size of the at least one crystal grain;
taking an average of the longitudinal size of each measured crystal grain the grain interface diagram as the transverse size of the crystal grain of the crystal; and
taking an average of the longitudinal size of each measured crystal grain in the grain interface diagram as the longitudinal size of the crystal grain of the crystal;
determining a process evaluation value of the poly-silicon thin film according to the transverse size and the longitudinal size of the crystal grain of the poly-silicon thin film;
determining an adjusted process parameter of the excimer laser annealing process according to the process evaluation value, and a set correspondence relationship between process evaluation values and adjusted process parameters; and
adjusting the current process parameter of the excimer laser annealing process to the adjusted process parameter, and subjecting an amorphous-silicon thin film to the excimer laser annealing process using the adjusted process parameter to form the poly-silicon thin film.

11. The method according to claim 10, wherein the process evaluation value is one or a combination of a difference between the transverse size and the longitudinal size of the crystal grain of the poly-silicon thin film, and a difference between an average of the transverse size and the longitudinal size of the crystal grain of the poly-silicon thin film, and a process specification value.

* * * * *